(12) United States Patent
Pyrzowski et al.

(10) Patent No.: US 11,684,303 B2
(45) Date of Patent: Jun. 27, 2023

(54) METHOD FOR IDENTIFICATION OF PATHOLOGICAL BRAIN ACTIVITY FROM SCALP ELECTROENCEPHALOGRAM

(71) Applicants: BIOSERENITY, Paris (FR); ICM (INSTITUT DU CERVEAU ET DE LA MOELLE ÉPINIÈRE), Paris (FR); APHP (ASSISTANCE PUBLIQUE—HÔPITAUX DE PARIS), Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); SORBONNE UNIVERSITE, Paris (FR)

(72) Inventors: Jan Pyrzowski, Paris (FR); Michel Le Van Quyen, Paris (FR); Jean-Eudes Le Douget, Paris (FR)

(73) Assignees: Bioserenity, Paris (FR); ICM (Institut Du Cerveau Et De La Moellle Épiniére), Paris (FR); APHP (Assistance Publique—Hôpitaux De Paris), Paris (FR); Centre National De La Recherche Scientifique, Paris (FR); INSERM (Institut National De La Santé Et De La Recherche Médicale), Paris (FR); Sorbonne Universite, Paris (FR)

( * ) Notice: Subject to any disclaimer, the term of this patent is extended or adjusted under 35 U.S.C. 154(b) by 343 days.

(21) Appl. No.: 16/499,445

(22) PCT Filed: Mar. 30, 2018

(86) PCT No.: PCT/EP2018/058292
§ 371 (c)(1),
(2) Date: Sep. 30, 2019

(87) PCT Pub. No.: WO2018/178333
PCT Pub. Date: Oct. 4, 2018

(65) Prior Publication Data
US 2021/0093247 A1    Apr. 1, 2021

(30) Foreign Application Priority Data

Mar. 31, 2017   (EP) .................................... 17164291

(51) Int. Cl.
A61B 5/00        (2006.01)
A61B 5/372      (2021.01)
(Continued)

(52) U.S. Cl.
CPC .............. *A61B 5/372* (2021.01); *A61B 5/291* (2021.01); *A61B 5/31* (2021.01); *A61B 5/4094* (2013.01); *A61B 5/7246* (2013.01)

(58) Field of Classification Search
None
See application file for complete search history.

(56) References Cited

U.S. PATENT DOCUMENTS 6,442,421 B1   8/2002  Le Van Quyen et al.
2002/0095099 A1  7/2002  Quyen et al.
(Continued)

FOREIGN PATENT DOCUMENTS

WO   WO2016/028888 A1   2/2016

OTHER PUBLICATIONS

Quyen et al. Anticipation of epileptic seizures from standard EEG recordings. 2001. (Year: 2001).*
(Continued)

*Primary Examiner* — Etsub D Berhanu
(74) *Attorney, Agent, or Firm* — Lee & Hayes, P.C.

(57) ABSTRACT

A computer-implemented method for detecting pathological brain activity patterns from a scalp electroencephalographic signal, the method including the steps of obtaining (A) an electroencephalographic signal as a function of multiple channels and time; identifying (C), for each channel, the zero-crossings of the electroencephalographic signal over a fixed threshold; generating a zero-crossing representation of at least a segment of the obtained electroencephalographic signal with the identified zero-crossings; obtaining (D) a reference family of real functions of time and channels from a zero-crossing statistical analysis of zero-crossing representation of pre-recorded electroencephalographic signals;
(Continued)

calculating (E) a matching score by comparing the zero-crossing representation of a segment of the electroencephalographic signal with at least one reference function from the reference family of functions; and computing the matching score as a function of time by sliding the at least one reference function from the reference family of functions over the electroencephalographic signal.

16 Claims, 5 Drawing Sheets

(51) Int. Cl.
*A61B 5/31* (2021.01)
*A61B 5/291* (2021.01)

(56) References Cited

U.S. PATENT DOCUMENTS

2002/0103512 A1  8/2002  Echauz et al.
2007/0249954 A1  10/2007  Virag et al.

OTHER PUBLICATIONS

International Search Report dated Jul. 2, 2018 and Written Opinion in corresponding International application No. PCT/EP2018/058292; 11 pages.
Jan Pyrzowski et al., "Interval analysis of interictal EEG: pathology of the alpha rhythm in focal epilepsy", Dec. 1, 2015 (Dec. 1, 2015), XP055407659, Retrieved from the Internet: URL:https://www.ncbi.nlm.nih.gov/pmc/articles/PMC4639771/ [retrieved on Sep. 18, 2017] the whole document, 10 pgs.
Zandi et al., "Predicting epileptic seizures in scalp EEG based on a variational Bayesian Gaussian mixture model of zero-crossing intervals." IEEE Transactions on Biomedical Engineering, vol. 60, No. 5, May 2013, 14 pgs.
Spyrou et al., "Detection of Intracranial Signatures of Interictal Epileptiform Discharges from Concurrent Scalp EEG" International journal of neural systems, vol. 26, No. 4 (2016) 1650016, 18 pgs.
Berg et al., "Revised Terminology and Concepts for Organization of Seizures and Epilepsies: Report of the ILAE Commission on Classification and Terminology, 2005-2009," 2010. Epilepsia (51(4):676-685.
Japanese Office Action dated Feb. 8, 2022 in JP Application No. 2019-553868, a foreign corresponding application of U.S. Appl. No. 16/499,445, 9 pages.

\* cited by examiner

METHOD FOR IDENTIFICATION OF PATHOLOGICAL BRAIN ACTIVITY FROM SCALP ELECTROENCEPHALOGRAM

CROSS REFERENCE TO RELATED APPLICATIONS

This application is a U.S. National Phase Application of International Patent Application No. PCT/EP2018/058292 filed Mar. 30, 2018, which claims priority to European Patent Application No. 17164291.1 filed Mar. 31, 2017, both of which are incorporated herein by reference in their entirety.

FIELD

The present invention relates to a system and a method for the analysis of the scalp electroencephalogram. In particular, the invention relates to a method for the identification of pathological brain activity patterns of a subject using a non-linear classification method.

BACKGROUND

Scalp electroencephalography, consisting in recording brain electrical activity with electrodes placed on the surface of the scalp, is a fundamental tool for diagnosis and research of neurological disorders including epilepsy.

Traditionally, clinical review of the scalp electroencephalogram relies on visual evaluation of the morphology and spatial distribution of recorded waveform patterns in multiple channels, which is often a time consuming and inefficient procedure. The present method is capable of automatically detecting pathological brain activity patterns such as low-amplitude scalp manifestations of interictal epileptiform discharges as well as other neurophysiological phenomena.

Epilepsy, a neurological disorder concerning about 1% of the population, is characterized by spontaneous occurrence of seizures. The identification of scalp and intracranial epileptic discharges during the time between seizures (the interictal period) has a major role in epilepsy diagnosis and monitoring response to pharmacological treatment. Interictal epileptiform discharges have been associated not only with epilepsy but also with conditions where seizures may represent a secondary manifestation (e.g. neuroinflammatory and neurovascular disorders) as well as with certain non-epileptic neurological conditions such as the early stage of Alzheimer's disease. Indeed, in some conditions, electroencephalographic patterns are highly-disease specific.

Simultaneous recording of scalp and intracranial electroencephalographic signal has shown that only a minority of interictal epileptiform discharges detected by intracranial electrodes are identifiable by visual inspection of the scalp electroencephalogram. Indeed, the scalp electroencephalogram is subject to signal attenuation, poor spatial resolution, noise and artefacts, which compromise the detection of the signals of interest. In contrast, intracranial electroencephalographic signals are obtained from electrodes placed in direct proximity of relevant brain structures by invasive surgical procedures.

Clinically significant patterns of electroencephalographic recordings other than interictal epileptiform discharges are also of interest and have been reported in literature. For example, the detection of pathological electroencephalographic patterns directly preceding epileptic seizures, the so-called preictal period, in epileptic subjects would allow for generation of an appropriate warning signal to allow their secure accommodation. The ability to differentiate epileptic from non-epileptic subjects, distinguish between different epilepsy subtypes or diagnose non-epileptic neurological conditions basing on electroencephalographic patterns other than interictal epileptiform discharges and electrographic seizures would expand the application of electroencephalography in general neurology.

Therefore, one of the major issues in the present context is the development of a method allowing for detection of pathological brain activity patterns from signals recorded with non-invasive scalp electroencephalography.

Several scientific publications and patents have been dedicated to overcome said technical issues.

U.S. Pat. No. 6,442,421, Zandi et al. (Predicting epileptic seizures in scalp EEG based on a variational Bayesian Gaussian mixture model of zero-crossing intervals. IEEE Transactions on Biomedical Engineering, 2013) and more recently, Spyrou et al. (Detection of Intracranial Signatures of Interictal Epileptiforim Discharges from Concurrent Scalp EEG. International journal of neural systems, 2016) and Pyrzowski et al. (Interval analysis of interictal EEG: pathology of the alpha rhythm in focal epilepsy. Scientific Reports, 2015) disclose automated methods to detect interictal epileptiform discharges and other pathological brain activity patterns.

Spyrou et al. discloses an automatic intracranial interictal epileptiform discharge detection algorithm based on a linear classifier. The algorithm employs multichannel pattern classification in order to classify the events in a subject-independent fashion. Time-frequency features analyzed by a binary classifier are obtained by a spectrogram method. Said binary classifier distinguishes segments of the scalp electroencephalographic signal associated with intracranial interictal discharges from those that are not associated with intracranial interictal discharges. However, linear signal analysis methods are less suitable for the analysis of electroencephalographic signals than non-linear methods. Furthermore, said linear classifier uses time-frequency features of the signal which may be sensitive to electroencephalographic signal artefacts such as those produced by eye movement.

U.S. Pat. No. 6,442,421 discloses a method able to detect changes in brain electrical activity of a subject allowing to anticipate epileptic seizures and therefore to differentiate between physiological and pathological brain activity patterns. The method disclosed in U.S. Pat. No. 6,442,421 detects a pathological preseizure state by comparing the on-line recorded electroencephalographic signal to a non-seizure reference state. However, this method is subject-dependent since said non-seizure state reference has to be computed individually for each subject and is limited to single-channel analysis which induces loss of information about the phase relations existing between different channels that have been recorded.

Pyrzowski et al. discloses a computational method for discrimination of subjects with focal epilepsy from non-epileptic subjects, the method comprising the following steps:

a) using a plurality of electrodes over a determined period of time $t_0$ acquire a plurality of electroencephalographic signals;

b) band-pass filtering of the individual channel signals with a zero-phase shift finite impulse response filter;

c) identifying the zero (e.g. isoelectric line) crossings in the pre-processed electroencephalographic signals by linear interpolation;

d) histogramming of time intervals between subsequent zero-crossing for each channel;

e) summing up histograms obtained from different channels;

f) estimating the standard statistic parameters and entropy measures of the time interval histogram as well as relative counts of fixed-length intervals; and g) classifying said electroencephalographic signals with the use of the parameters monitored in f).

Pyrzowski et al. discloses a binary classification method. In particular, Pyrzowski et al. discloses a method for classifying interictal electroencephalographic recordings that is based on interval analysis. The principle consists in defining the histogram of time interval between subsequent zero-crossing points independently for multiple channels. The features of interest are calculated from the histogram representing a segment of the electroencephalographic recording that is to be classified. The classification allows to distinguish subjects with epilepsy from non-epileptic controls.

However, as U.S. Pat. No. 6,442,421, the method disclosed by Pyrzowski et al., in particular steps d) and e), induces loss of information about the phase relations existing between different channels that have been recorded.

Zandi et al. discloses a method for detecting pathological brain activity patterns allowing to predict seizures in a subject. Said method is also based on the analysis of zero-crossing interval histograms obtained from the scalp electroencephalogram. However, as in U.S. Pat. No. 6,442,421, this method is subject-dependent since the seizure is predicted by analyzing the similarities between the current electroencephalographic signal and an appropriate preictal and interictal reference obtained from the same subject.

In the present invention, the detection of pathological brain activity patterns (such as interictal epileptiform discharges) relies on the computation of a matching score reflecting the similarities between a segment of the electroencephalographic signal under analysis and a reference state which is typical for a pathological condition.

The present invention discloses an improved computer-implemented method for detection of pathological brain activity patterns in a subject. In the present invention, the electroencephalographic recording of a subject is evaluated with respect to a reference pathological state using a non-linear classification method. The method of the present invention uses only phase information of the electroencephalographic signal reducing the influence of signal artefacts and amplitude noise, providing improved performance compared to the method disclosed by Spyrou et al.

Furthermore, in the present invention the reference state is generalized for a specific pathological condition and can be used for different subjects who are suspected to present said specific pathological condition. Therefore, the present invention allows a much wider application than only epilepsy and overcomes the restriction of computing patient specific references as in U.S. Pat. No. 6,442,421 and Zandi et al.

SUMMARY

The present invention relates to a computer-implemented method for detecting pathological brain activity patterns from a scalp electroencephalographic signal, the method comprising the steps of:

a) obtaining an electroencephalographic signal as a function of multiple channels and time, identifying, for each channel;

b) identifying, for each channel, the zero-crossings of the electroencephalographic signal over a fixed threshold;

c) generating a zero-crossing representation of at least a segment of the obtained electroencephalographic signal with the identified zero-crossings;

d) obtaining a reference family of real functions of time and channels from a zero-crossing statistical analysis of zero-crossing representation of pre-recorded electroencephalographic signals;

e) calculating a matching score by comparing said zero-crossing representation of a segment of the electroencephalographic signal with at least one reference function from the reference family of functions; and f) computing the matching score as a function of time by sliding the at least one reference function from the reference family of functions over the electroencephalographic signal.

The present invention relates to a computer implemented method for detecting pathological brain activity patterns from a scalp electroencephalographic signal, the method comprising the steps of:

a) obtaining an electroencephalographic signal as a function of multiple channels and time;

b) identifying, for each channel, the zero-crossings of the electroencephalographic signal over a fixed threshold;

c) generating a zero-crossing representation of at least a segment of the obtained electroencephalographic signal with the identified zero-crossings;

d) obtaining a reference family of real functions of time and channels from a zero-crossing statistical analysis of the zero-crossing representation of pre-recorded electroencephalographic signals, wherein said step of obtaining the reference family comprises the steps:

i. obtaining simultaneous recordings of at least one scalp electroencephalographic signal and/or and at least one intracranial electroencephalographic signal of predefined length;

ii. analyzing statistically the zero-crossings of at least one scalp electroencephalographic signal with respect to at least one feature of the obtained recordings; and iii. computing the reference family of functions from the statistical analysis;

e) calculating a matching score by comparing said zero-crossing representation of a segment of the electroencephalographic signal with at least one reference function from the reference family of functions; and computing the matching score as a function of time by sliding the at least one reference function from the reference family of functions over the electroencephalographic signal.

According to one embodiment, the computer-implemented method further comprises a step of evaluating a matching score.

According to one embodiment, the step b) is preceded by a filtering step comprising filtering the electroencephalographic signal with a zero-phase shift bandpass filter.

According to one embodiment, the filtering step is followed by the step of dividing the electroencephalographic signal into non-overlapping consecutive segments of fixed length.

According to one embodiment, the matching score relative to an electroencephalographic segment for one reference function T centered in to is defined by the formula:

$$S_T(t_0) = \sum_{k \in K} \sum_{t \in \Phi(k,t_0)} T_k(t - t_0),$$

wherein the first sum runs over the set of analyzed channels $k \in K$ and the second one runs over a defined subset $\phi(k, t_0)$ of zero-crossings for each channel k of the electroencephalogram segment surrounding to.

According to one embodiment, the matching score is calculated for a set of functions belonging to one reference family of functions, producing a respectively indexed set of matching scores for any given to.

According to one embodiment, calculating the matching score for a continuously indexed reference family of functions, produces a continuous matching score function for any given to.

According to one embodiment, the analysis of the electroencephalographic signal is performed by computing the matching score for two reference functions issued from two different reference families of functions.

According to one embodiment, the step f) is performed by setting a binary criterion on the matching score such as the comparison of the matching score to a fixed threshold.

According to one embodiment, the method differentiates physiological electroencephalographic signal from electroencephalographic signal comprising pathological brain activity patterns.

According to one embodiment, the differentiation between physiological electroencephalographic signal and electroencephalographic signal comprising pathological brain activity patterns is performed in real time.

The present invention further relates to a method for constructing the reference family of functions comprising the steps of obtaining simultaneous recordings of at least one scalp electroencephalographic signal and/or and at least one intracranial electroencephalographic signal of predefined length, analyzing statistically the zero-crossings of at least one scalp electroencephalographic signal with respect to at least one feature of the obtained recordings and computing the reference family of functions from the statistical analysis.

The present invention further relates to a method for constructing the reference family of functions comprising the steps of obtaining recordings at least one scalp electroencephalographic signal of predefined length and deriving a reference family of functions by optimizing the parameters of a mathematical function according to the characteristics of the obtained electroencephalographic signal recordings.

The present invention also relates to a system for detecting pathological brain activity patterns, the system comprising a data processing system comprising means for carrying out the steps of the computer-implemented method according to anyone of the embodiments described hereabove.

The present invention also relates to a computer program product for detecting pathological brain activity patterns, the computer program product comprising instructions which, when the program is executed by a computer, cause the computer to carry out the steps of the method.

The present invention also relates to a computer-readable storage medium comprising instructions which, when the program is executed by a computer, cause the computer to carry out the steps of the computer-implemented method according to anyone of the embodiments described hereabove.

According to one embodiment, the computer-readable storage medium further comprises at least one reference family of functions.

In the present invention, the following terms have the following meanings:

"Approximately" refers to a value within 10% variation, preferably within 5% variation from the reference.

"Binary classifier" refers to a system classifying the objects of a given set into two classes on the basis of a classification rule.

"Epoch" refers to a determined period of the electroencephalographic signal that is analyzed independently. Epochs are not overlapping.

"Physiological activity pattern" refers to the normal electrical activity of the brain such as for examples the occipital alpha rhythm, sleep spindles, K-complexes and slow waves of sleep.

"Pathological activity pattern" refers to an abnormality that may be present in a brain electrical activity. The abnormality of brain electrical activity may refer to a spectrum characteristic such as amplitude, phase and frequency or any pattern that can be detected in the brain electrical signals. The abnormality may also result from any operations on the brain electrical signals such as comparison, correlation, etc., as for example operation on a predefined time window or on a predefined frequency band. In some cases, the abnormality is defined with respect to an absolute reference such as a database reference or with a relative reference by comparing properties of the signal on an acquired sequence.

In some specific cases, "Pathological activity pattern" refers to brain electrical activity that is present in brain disorders and that is different from physiological activity, such as for example interictal epileptiform discharges and electrographic seizures, known to be characteristic for epilepsy.

"Electroencephalogram" refers to the record of the electrical activity of the brain of a subject.

"Family of functions" refers to an indexed collection of functions $\{f_i\}_{i \in I}$ wherein the indexing set I is discreet or continuous.

"Interictal epileptiform discharges" refers to discharges that occur between seizures and are characteristic for an epileptic brain.

"Integrable function" refers to a function f: $[a,b] \to \mathbb{R}$ for which exists a number L such that for any $\varepsilon > 0$ there exists a division $\Delta$ such that $L - \varepsilon < S(f, \Delta) < L + \varepsilon$.

"Intracranial electroencephalogram" refers to the record of the electrical activity of the brain of a subject, obtained by electrodes implanted intracranially.

"Subject" refers to a mammal, preferably a human.

"Preseizure state" refers to a state preceding (and heralding) a seizure for minutes to hours.

"Real function" refers to a mapping or a function whose domain and codomain are subsets of the set of real numbers $\mathbb{R}$ "Receiving-operating-characteristics" refers to a graphical plot that illustrate the performances of a binary classifier system as its discrimination threshold is varied. The curve is created by plotting the True Positive Rate against the False Positive Rate.

"Scalp electroencephalogram" refers to the record of the electrical activity of the brain of a subject, obtained by electrodes applied on the scalp.

"Set of functions" refers to a family of functions for which the indexing set is discrete.

"Seizure" refers to a transient occurrence of signs and/or symptoms due to abnormal, excessive and synchronous neuronal activity in the brain.

"Spike" distinctive sharp waveform, distinguished from background activity, and resembling those recorded in proportion human subjects suffering from epileptic disorders.

"Waveform" refers to the shape and form of a signal segment.

"Zero-phase shift bandpass filter" refers to a filter that passes frequencies within a certain range and rejects frequencies outside that range, in the special case of its phase slope equal to zero.

"Obtaining": refers to computer implemented operations such as calculating or generating or receiving any other equivalent operation

DETAILED DESCRIPTION

This invention relates to a computer-implemented method allowing the detection of pathological brain activity patterns from analysis of a scalp electroencephalographic signal of a subject. Said pathological brain activity patterns are characterized by the presence of waveforms specific for the brain pathology under examination. According to one embodiment, the computer-implemented method of the present invention identifies segments of the scalp electroencephalographic signal presenting said pathological brain activity patterns by calculating a matching score, obtained by comparing each segment of the studied signal to a reference family of functions associated with a pathological state. Said matching score is then evaluated according to the pathology under analysis.

According to one embodiment, the present invention comprises a preliminary step of receiving an electroencephalographic signal of a subject from multiple channels and as a function of time.

Figure 1:
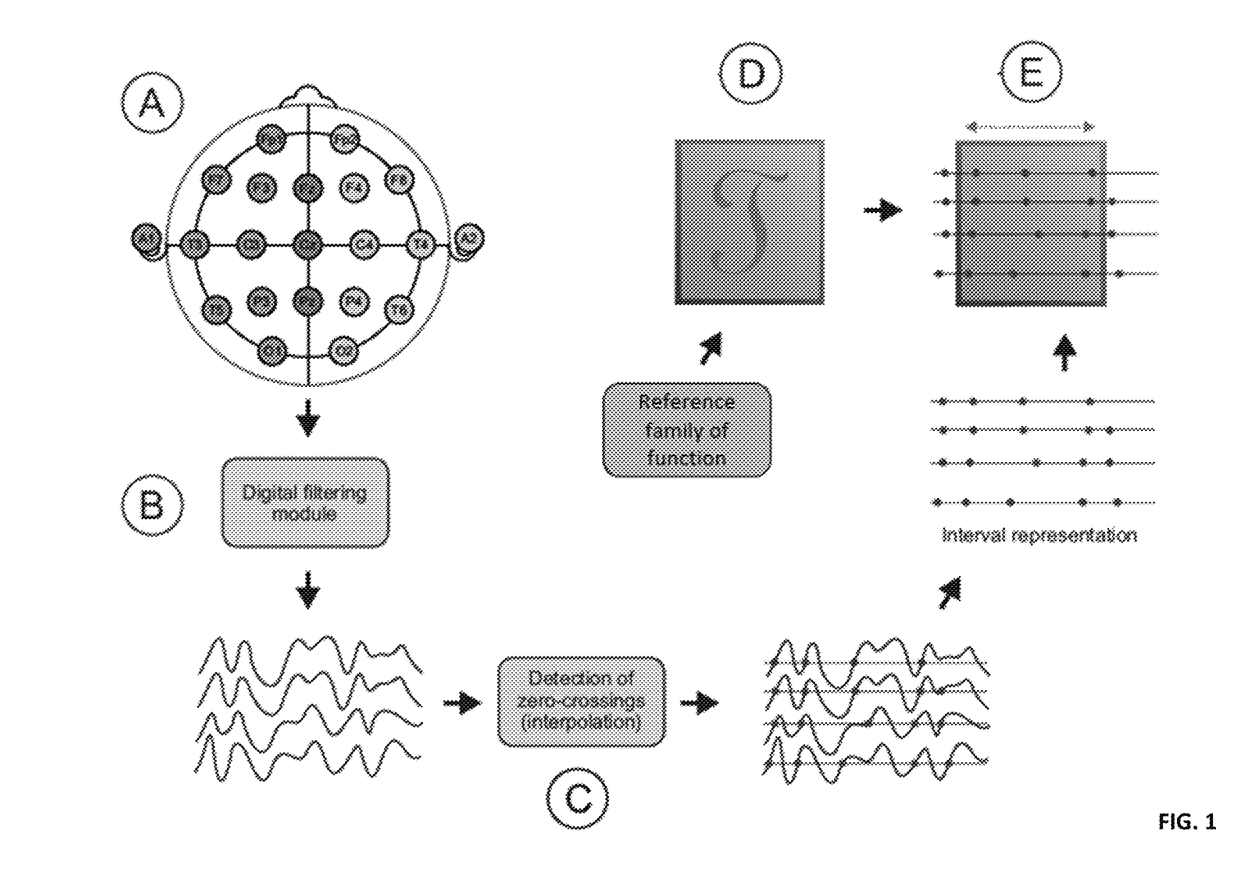
FIG. 1 is a flow diagram illustrating the different steps of the method of the invention, for real-time detection of pathological brain activity patterns from an electroencephalographic signal.

According to one embodiment, the electroencephalographic signal received is recorded from a plurality of electrodes, positioned onto predetermined areas of the scalp of the subject in order to obtain a multi-channel electroencephalographic signal. According to one embodiment, the electrodes are placed on the scalp according to the 10-10 or 10-20 system or dense-array positioning (FIG. 1, A).

According to one embodiment, the electroencephalographic signal received is obtained with a standard recording module with sampling frequency of at least 200 Hz.

According to one embodiment, the electroencephalographic signal is received in real time. According to another embodiment, the electroencephalographic signal is recorded during a predefined period of time and stored in a storage medium. According to another embodiment, the electroencephalographic signal is obtained from a database, such as for example a medical database.

According to one embodiment, the electroencephalographic signal from individual scalp electrodes is digitally filtered with a bandpass filter selecting a specific range of frequencies (FIG. 1, B); a skilled artisan would be able to select a suitable range of frequencies. According to one embodiment the bandpass filter is a zero-phase shift bandpass filter.

According to one embodiment, the computer-implemented method comprises the step of dividing the prerecorded electroencephalographic signal into non-overlapping consecutive segments of fixed length also called epochs. According to one embodiment, said fixed length of segments is of the order of tens of seconds. For tens of seconds to has be understood a time lapse of 10, 20, 30, 40, 50 or 60 s for example.

According to one embodiment, the method of the present invention identifies, for each channel, the so-called zero-crossings of the electroencephalographic signal, over a fixed threshold (FIG. 1, C). Said fixed threshold may be the isoelectric line, corresponding to an amplitude of zero.

According to one embodiment, the zero-crossings are identified as the points wherein the voltage value passes from below the fixed threshold to above the fixed threshold. According to another embodiment, the zero-crossings are identified as the points wherein the voltage value passes from above the fixed threshold to below the fixed threshold. According to another embodiment, the zero-crossings are identified as the points wherein the voltage value passes from the fixed threshold regardless weather from below to above or from above to below.

According to one embodiment, the computer-implemented method for detecting pathological brain activity patterns used in the present invention relies on a reference family of functions $\{T\} \equiv \{T_l\}_{l \in L}$ obtained from predefined electroencephalographic signals. Said reference functions $T \in \{T\}$ which comprise the family indexed by the variable $l \in L$, are real functions of time and of channels:

$$\forall_{l \in L} \{T_l : (k, t) \to \mathbb{R}\},$$

where t represents time and k the channel identifier (e.g. name or number of the channel). In one embodiment, said reference functions are time-integrable. The predefined electroencephalographic signals from which the reference family of functions is obtained are chosen to contain patterns of brain waveforms which are specific for a single pathology.

According to one embodiment, the computer-implemented method comprises at least one reference family of functions (FIG. 1, D). According to one embodiment, at least one reference family of functions is stored in a storage medium. According to one embodiment, the reference family of functions referencing one pathology is computed beforehand from the electroencephalographic signals that contains patterns of brain waveforms associated with said pathology.

According to one embodiment, the computed-implemented method for detecting pathological brain activity patterns, comprises the step of calculating the matching score by comparing a segment of the electroencephalographic signal with at least one of the function of the reference family of functions.

According to one embodiment, the matching score $S_T(t_0)$ relative to an electroencephalogram segment for one reference function T (a single member of the reference family of functions) centered in to is defined by the formula:

$$S_T(t_0) = \sum_{k \in K} \sum_{t \in \Phi(k, t_0)} T_k(t - t_0), \quad (1)$$

wherein the first sum runs over the set of all analyzed channels $k \in K$ and the second one runs over a defined subset $\Phi(k, t_0)$ of zero-crossings for each channel k of the electroencephalogram segment surrounding $t_0$.

According to one embodiment, the defined subset of zero-crossings $\Phi(k, t_0)$ consists of all zero-crossings identified in channel k in the studied segment and is independent of $t_0$.

According to another embodiment, the defined subset of zero-crossings $\Phi(k, t_0)$ consists of all zero-crossings in channel k for which $|t-t_0|<\tau$ holds for a fixed value of z. According to another embodiment, the defined subset of zero-crossings $\Phi(k, t_0)$ consists of n zero-crossings that precede $t_0$ and m zero-crossings that succeed to in channel k with n and m fixed.

According to one embodiment, the matching score as a function of time $t_0$ is calculated over the recorded electroencephalographic signal by sliding the at least one reference function along the spatio-temporal set of zero-crossings in small intervals of to (FIG. 1, E). For a small interval, it has to be understood a time interval of the order of the milliseconds, such as for example 1, 2, 3, 4, 5, 6, 7, 8, 9 or 10 milliseconds.

According to the embodiment using a single reference function, the matching score is a real number associated to each time $t_0$ on which the reference function is centered when it is slid in said small intervals.

According to one embodiment, the analysis of the entire recording of the electroencephalographic signal is performed by computing the matching score for two reference functions $T^{(1)}$ and $T^{(2)}$: $\{T^{(1)}T^{(2)}\} \to \{S_{T^{(1)}}(t_0), S_{T^{(2)}}(t_0)\}$ for a given $t_0$.

According to one embodiment the matching score is calculated for a discrete set of reference functions belonging to one reference family of functions. The use of said discrete set of functions produces a respectively indexed set of matching scores, each of which is a real function of time $t_0$:
$\{T^{(l)}\}_{l \in \mathbb{Z}} \to \{S^{(l)} : t_0 \to \mathbb{R}\}_{l \in \mathbb{Z}}$.

According to another embodiment, the matching score is calculated for a continuously indexed reference family of functions, which produces a continuous matching score $\{T_l\}_{l \in \mathbb{R}} \to \{S(l, t_0)\}_{l \in \mathbb{R}}$, a real function of time $t_0$ and the indexing variable l.

In one of the multiple possible application of the method of the present invention, the interpretation of the matching score associated with the reference family of functions may depend on a clinical context and the design of the reference family of functions. According to an alternative application, the interpretation of the matching score may depends only on the design of the reference family of functions.

According to one embodiment, the present invention comprises the act of detecting pathological brain activity patterns by setting a binary criterion on the matching score. Said binary criterion depends on the reference family of functions used and on the clinical context.

According to one embodiment, said binary criterion is comparing the matching score obtained for each time $t_0$ to a threshold, wherein said threshold depends on the reference family of functions used and on the clinical context.

According to one embodiment said binary criterion is comparing the supremum of the matching score obtained for each time $t_0$ over the reference family of functions to a threshold, where said threshold depends on the reference family of functions used and on the clinical context. In such a context, we refer to the supremum as to a compound matching score.

According to another embodiment, the act of detecting pathological brain activity further comprises the step of summing up the matching score obtained for each time $t_0$ over the one or more predefined epochs of the electroencephalographic recording to calculate a cumulative matching score. According to one embodiment said binary criterion comprises comparing the cumulative matching score to a threshold, where said threshold depends on the reference family of functions used, on the duration of the epochs and on the clinical context.

According to one embodiment, the method of the present invention allows to differentiate a physiological electroencephalographic signal from an electroencephalographic signal containing pathological brain activity patterns. According to one embodiment, said differentiation is performed in real-time. According to one embodiment, the matching score and/or detected pathological brain waveforms that are identified are graphically displayed on a monitor. The pathological brain waveforms identified may be highlighted in order to facilitate the review of the electroencephalographic signal.

According to one embodiment, real-time monitoring of the scalp electroencephalographic signal allows to determine if the subject is in a preseizure state. Said identification of a preseizure state may alert the subject and allow his secure accommodation.

The present invention further comprises a method for constructing a reference family of functions to allow the detection of specific pathological brain activity patterns in a subject.

According to one embodiment, the method for constructing the reference family of functions comprises a preliminary step of obtaining recordings of at least one scalp electroencephalographic signal of predefined length.

According to an alternative embodiment, said preliminary step consists of obtaining simultaneously at least one scalp electroencephalographic signal and at least one intracranial electroencephalographic signal of predefined length.

According to one embodiment, at least one feature of said electroencephalographic signals is analyzed statistically.

According to one embodiment, said at least one feature of the electroencephalographic signals is the timing of particular brain waveforms. According to another embodiment, said at least one feature of the electroencephalographic signals is the clinical diagnosis or other clinically relevant data associated with the subjects from whom the electroencephalographic signals were obtained.

According to one embodiment, the method of constructing the reference family of functions computes the reference family of functions directly from the statistical analysis.

According to one embodiment, histogramming of zero-crossing delays with respect to the timing of a particular brain waveform is used to compute the reference family of functions.

According to another embodiment, the method of constructing the reference family of functions derives a reference family of functions by optimizing the parameters of a mathematical function according to the features of the obtained electroencephalographic recordings.

According to one embodiment, the optimization of the mathematical function's parameters is based on the clinical diagnosis associated with the subjects from whom the electroencephalographic signals were obtained, such as for example to maximize discriminative power for the detection of epileptic subjects as opposed to non-epileptic control subjects. According to another embodiment, said optimization is carried out in order to maximize discriminative power for the differentiation of electroencephalographic signal obtained from subjects with specified epilepsy subtypes.

According to another embodiment, said optimization is carried out in order to maximize discriminative power for the detection of electroencephalographic signals associated with a specific non-epileptic condition in the subjects.

According to another embodiment, the optimization of the mathematical functions' parameters is based on the known timings of occurrences of particular pathological brain activity patterns, as for example of electrographic seizures. According to one embodiment, said optimization is carried out in order to maximize discriminative power for the detection of epochs directly preceding a seizure (e.g. the preseizure state).

According to another embodiment, said optimization is carried out in order to maximize discriminative power for the detection of specific states of vigilance such as for example of sleep stages.

According to one embodiment, said optimization is carried out using mathematical methods derived from the machine-learning discipline.

According to one embodiment, the reference family of functions are subject to further arbitrary mathematical transformations. The skilled artisan would be able select the appropriate transformations on a heuristic basis in view of a given clinical context.

Examples of neurological disorders associated with the presence of pathological brain activity patterns in the electroencephalographic signal that can be detected by the present computer-implemented method include but are not limited to: all of epileptic conditions, neurodegenerative disorders (e.g. Alzheimer's disease, vascular dementia, Lewy body dementia, fronto-temporal lobar dementia), toxic or metabolic disorders (e.g. hepatic encephalopathy), anoxic encephalopathy, neuroinflammatory disorders (e.g. systemic lupus erythematosus with brain involvement), Creutzfeldt-Jacob disease and other prior disorders, neuroinfectious disorders (e.g. herpes simplex encephalitis, Subacute sclerosing pan-encephalitis, HIV encephalitis), neurovascular disorders (e.g. ischemic and hemorrhagic stroke including subarachnoid hemorrhage), headache (e.g. migraine, tension type headache), amnesic states (e.g. transient global amnesia), psychiatric disorders (e.g. schizophrenia, depression) and other specific pathological states such as coma, vegetative state and minimally conscious state.

According one embodiment of the present invention, the pathological brain activities arise from an epileptic condition.

The ILAE (International League Against Epilepsy) has published in 2010 a revised classification of epileptic conditions (Berg et al, Epilepsia, 51(4):676-685, which is herein incorporated by reference). According to said classification, epileptic conditions may be classified according to the seizure type (generalized seizures, focal seizures, or spasms), etiology (genetic [including idiopathic], structural/metabolic [or symptomatic], or unknown cause [or cryptogenic]), age at onset, cognitive and developmental antecedents and consequences, motor and sensory examinations, EEG features, provoking or triggering factors, and/or patterns of seizure occurrence with respect to sleep.

Examples of epileptic conditions include, but are not limited to, epileptic encephalopathies, early infantile epileptic encephalopathies (EIEEs), Dravet syndrome, benign familial neonatal epilepsy (BFNE), early myoclonic encephalopathy (EME), Ohtahara syndrome, epilepsy of infancy with migrating focal seizures, West syndrome, Myoclonic epilepsy in infancy (MEI), benign infantile epilepsy, benign familial infantile epilepsy, myoclonic encephalopathy in non-progressive disorders, febrile seizures plus (FS+), Panayiotopoulos syndrome, epilepsy with myoclonic atonic seizures, benign epilepsy with centrotemporal spikes (BECTS), autosomal-dominant nocturnal frontal lobe epilepsy (ADNFLE), late onset childhood occipital 5 epilepsy, epilepsy with myoclonic absences, Lennox-Gastaut syndrome, epileptic encephalopathy with continuous spike-and-wave during sleep (CSWS), Landau-Kleffner syndrome (LKS), childhood absence epilepsy (CAE), juvenile absence epilepsy (JAE), juvenile myoclonic epilepsy (JME), epilepsy with generalized tonic-clonic seizures alone, progressive myoclonus epilepsies (PME), autosomal dominant epilepsy with auditory features (ADEAF), focal epilepsies, familial and sporadic epileptic condition, lesional and non-lesional epileptic condition, other familial temporal lobe epilepsies (FTLE) (such as, for example, mesial form of FTLE, familial mesial temporal lobe epilepsy (FMTLE) or familial lateral temporal lobe epilepsy (FLTLE), familial focal epilepsy with variable foci (FFEVF, childhood to adult), familial partial epilepsy with variable foci (FPEVF), benign familial partial epilepsies of childhood, reflex epilepsies, mesial temporal lobe epilepsy with hippocampal sclerosis (MTLE with HS), temporal lobe epilepsy, idiopathic generalized epilepsy (IGE), Rasmussen syndrome, gelastic seizures with hypothalamic hamartoma, hemiconvulsion-hemiplegia-epilepsy, neurocutaneous 20 syndromes (tuberous sclerosis complex, Sturge-Weber and the like), epilepsies attributed to malformations of cortical development, tumor, infection or trauma, benign neonatal seizures (BNS), febrile seizures (FS), generalized epilepsy with febrile seizures plus (GEFS+) and epileptic conditions including specific syndromes such as ADNFLE, FTLE, FFEVF, rolandic epilepsies and malignant migrating partial seizures of infancy.

In one embodiment of the present invention, the epileptic condition is focal epilepsy.

In an alternative embodiment of the present invention, the epileptic condition is generalized epilepsy.

In one embodiment of the present invention, the epileptic condition is temporal lobe epilepsy.

In an alternative embodiment of the present invention, the epileptic condition is frontal lobe epilepsy.

In one embodiment of the present invention, the epileptic condition is mesial temporal lobe epilepsy with hippocampal sclerosis.

In one embodiment of the present invention, the epileptic condition is focal epilepsy attributed to malformations of cortical development.

The present invention also relates to a system for detecting pathological brain activity patterns, the system comprising a data processing system comprising means for carrying out the steps of the computer-implemented method according to anyone of the embodiments described hereabove.

The present invention further relates to a computer program product for detecting pathological brain activity patterns, the computer program product comprising instructions which, when the program is executed by a computer, cause the computer to carry out the steps of the computer-implemented method according to anyone of the embodiments described hereabove.

The present invention further relates to a computer-readable storage medium comprising instructions which, when the program is executed by a computer, cause the computer to carry out the steps of the computer-implemented method according to anyone of the embodiments described hereabove.

According to one embodiment, the present invention relates to a device comprising a plurality of electrodes positioned onto predetermined areas of the scalp of a subject recording multi-channels electroencephalographic signal through said plurality of electrodes and the system for detecting pathological brain activity patterns.

According to one alternative aspect, the present invention relates to a computer-implemented method for detecting brain activity patterns from a scalp electroencephalographic signal, the method comprising the steps of:

a) obtaining an electroencephalographic signal as a function of multiple channels and time;
b) identifying, for each channel, the zero-crossings of the electroencephalographic signal over a fixed threshold;
c) obtaining a reference family of real functions of time and channels from zero-crossing statistical analysis of zero-crossing of the electroencephalographic signals;
d) calculating a matching score by comparing a zero-crossing representation of a segment of the electroencephalographic signal with at least one reference function from the reference family of functions; and
e) computing the matching score as a function of time by sliding the at least one reference function from the reference family of functions over the electroencephalographic signal.

According to one embodiment, the matching score is evaluated.

According to another embodiment, the matching score is calculated for multiples reference functions.

According to an alternative embodiment or to a combined embodiment with previous embodiments, the matching score is an output of the method. In one embodiment, the matching score is graphically represented on a display screen or a printed paper. Said graphical representation may be a refence mark which is overlapped to a graphical representation of electroencephalographic signals. The position, the size and/or the color of such reference mark may be function of the matching score value calculated for a given electroencephalogram epoch. According to one embodiment wherein the matching score is calculated in real time, the matching score is outputted as a sound. The modulation of the intensity and/or the frequency of said sound may be function of matching score value. In such an embodiment, the sound outputted to be heard by the subject and/or medical stuff. In one illustrative example, said modulated sound reaching a predefined intensity and/or frequency may be used as indicator to instruct the user and/or the medical stuff to start a procedure such as a safety procedure. Said safety procedure may consist for example in making the subject sit on a chair or lie on a bed.

In one embodiment, the matching score is stored on a computer readable storage medium, transitory or non-transitory.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

A—Apparatus;
B—Signal filtering for each channel;
C—Detection of the zero-crossings;
D—Reference family of functions;
E—Calculation of the matching score as a function of time;
1—Scalp channels;
2—Intracranial channel;
3—Time interval between the intracranial spike and the previous scalp zero-crossing;
4—Time interval between the intracranial spike and the following scalp zero-crossing;
5—Prominence;
6—Duration of the waveform;
7—Sharpness;
8—Intracranial spike;

100—Graphic representation of a selected reference function;

200—Matrix of AUC($T^{(I)}$, l') values.

EXAMPLES

The present invention is further illustrated by the following examples.

Example 1

Materials and Methods

Material

A computer-implemented method according to the present invention was used to detect pathological brain activity patterns in 16 subjects. Said 16 subjects present epilepsy, for which intracranial interictal epileptiform discharges are a characteristic pathological brain activity pattern.

Therefore, the reference family of functions was constructed to allow detection of intracranial interictal epileptiform discharges from the scalp electroencephalographic signal.

Figure 2:
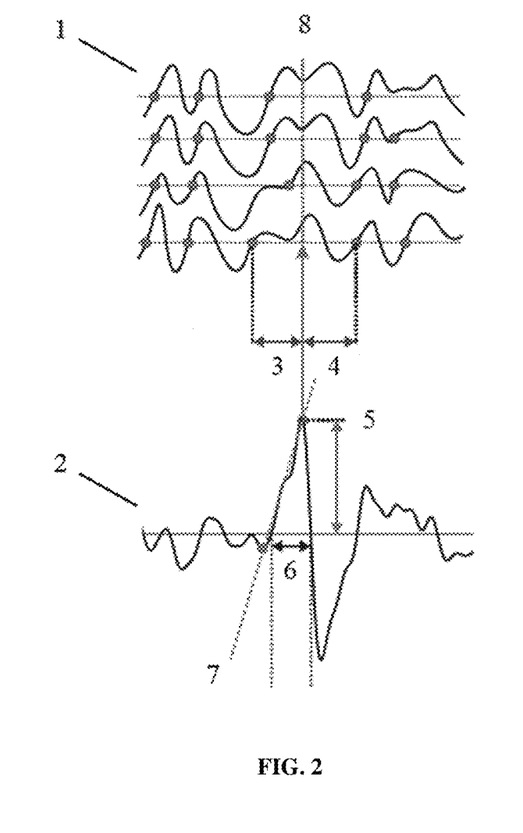
FIG. 2 is a schematic representation of scalp channels showing zero-crossing points and their relationship to the timing of an interictal epileptiform discharge, simultaneously recorded in an intracranial channel.

The prerecorded simultaneous intracranial electroencephalographic signal and scalp electroencephalographic signal were chosen from the medical database Epilepsiae. The prerecorded signals were chosen from 16 patients with temporal lobe epilepsy for which, as shown in FIG. 2, simultaneous scalp electroencephalographic signal (1) and intracranial electroencephalographic signal (2) were acquired. Only patients with full 10-20 scalp coverage supplemented with true anterior-temporal electrodes (T1 and T2) were included in the example. The prerecorded signals ranged in length from 51 to 346 hours.

The clinical and demographic details of the subjects are specified in the Table 1 below:

TABLE 1

| Patient | Gender | Age | Age at epilepsy onset | Focus location | Etiology |
|---|---|---|---|---|---|
| 1 | female | 47 | 0 | Right medial temporal Right lateral temporal | Hippocampal sclerosis |
| 2 | female | 32 | 1 | Left medial temporal | Malformation hippocampal sclerosis |
| 3 | female | 11 | 3 | Right medial temporal | Malformation Hippocampal sclerosis |
| 4 | female | 48 | 22 | Bilateral temporal | Idiopathic |
| 5 | male | 21 | 5 | Right medial temporal Right lateral temporal | Genetic risk |
| 6 | male | 17 | 1 | Left medial temporal Left lateral temporal Left temporal | Malformation Hippocampal sclerosis |
| 7 | male | 13 | 0 | Left medial temporal Left lateral temporal | Hippocampal sclerosis Focal cortical dysplasia |
| 8 | female | 22 | 18 | Left lateral temporal | Focal cortical dysplasia |
| 9 | male | 18 | 11 | Left basal temporal Left lateral temporal Right basal temporal | Malformation |
| 10 | male | 42 | 16 | Right lateral temporal | Malformation |
| 11 | female | 63 | 30 | Left medial temporal Right temporal | Tumor |
| 12 | female | 27 | 10 | Left temporal | Hippocampal sclerosis |
| 13 | male | 23 | 18 | Left medial temporal | Malformation |
| 14 | female | 14 | 13 | Left temporal Left lateral temporal | Cryptogenic |
| 15 | male | 15 | 6 | Right basal temporal | Malformation |
| 16 | male | 34 | 10 | Right medial temporal | Hippocampal sclerosis |

Methods

For each subject, the recordings from intracranial channels were segmented into non-overlapping 60 second epochs. The epochs registered within 30 minutes from any annotated seizure were excluded from further analysis. For each subject two validation subsets $V_1$ and $V_2$ of approximately 10' epochs were chosen using stratified sampling and the remaining epochs were used for reference function design (NV, non-validation epochs). Said two validation subsets $V_1$ and $V_2$ were used to evaluate the performances of the computed reference family of functions.

For each non-validation epoch, the simultaneous intracranial signal (2) was first transformed into local bipolar montage. For bipolar montage, it has to be understood a montage comprising two electrodes per each channel, so as to have in general a different reference electrode for each channel. According to one embodiment, said bipolar montage is obtained by referencing pairs of adjacent contacts of subdual grid, subdural strip or depth electrode starting from the deepest electrode.

Then for every channel the signal was initially passed through a digital bandpass filter set at [3-45] Hz. All maxima and minima of the filtered signal were identified numerically. For each of said maxima and minima the values of prominence $p_k$ (5) and sharpness $s_k$ (7) were calculated according to the following definitions:

$$p_k = \left| a_k - (a_k - a_{k-1}) \cdot \frac{(t_k - t_{k-1})}{(t_{k+1} - t_{k-1})} \right|, \qquad (2)$$

$$s_k = \left| \frac{(a_k - a_{k-1})}{(t_k - t_{k-1})} \right| + \left| \frac{(a_{k+1} - a_k)}{(t_{k+1} - t_k)} \right|, \qquad (3)$$

wherein $a_k$ and $t_k$ are respectively the amplitude and the timing of the k-th maximum or minimum.

The maxima and the minima associated with prominence and sharpness values above predefined thresholds (prominence superior to 3 standard deviations within the currently studied epoch and sharpness superior to 5 standard deviations within the studied epoch) were identified as spikes (8) if the extrapolated duration of the waveform (6) did not exceeded 200 milliseconds. The prominence and sharpness thresholds were chosen to allow for high specificity of detection.

The zero-crossings were calculated for each scalp channel l. For each subject, a reference function $T^{(l)}$ was derived for every intracranial channel l using the non-validation epochs, selected as described above. Every intracranial channel l was studied separately and gave rise to its individual reference function $T^{(l)}$.

For every intracranial spike (8) detected in the intracranial channel l within a given epoch j and for a given scalp channel k was calculated the time interval between said intracranial spike (8) and the zero-crossing in the scalp signal l preceding it (3). These values were then histogrammed in 10 milliseconds bins and normalized to estimate the distribution of the waiting time $P_{jk}^{pre}$ for each channel.

For every intracranial spike (8) in the intracranial channel l within a given epoch j and a given scalp channel k the time interval between each intracranial spike (8) and the scalp zero-crossing following it (4) was calculated. These values were then histogrammed in 10 milliseconds bins and normalized to estimate the distribution of the waiting time $P_{jk}^{post}$ for each channel.

The normalized distributions of time intervals i between two subsequent zero-crossings, the so-called interval distributions $P_{jk}^{interv}$, were also estimated for each epoch j and channel k by histogramming said intervals in 10 milliseconds bins. Said interval distributions were then used to estimate a null waiting time distribution for each channel k under the assumption that the sequences of intervals in scalp channels correspond, within each 60-second epoch, to independent stationary renewal processes, characterized for each epoch j and channel k only by $P_{jk}^{interv}$. It follows that for any uniformly sampled random point in time the waiting time until the next zero-crossing is distributed according to null waiting time distribution $P_{jk}^{null}$:

$$P_{jk}^{null}(t) = \int_{i=t}^{\infty} \frac{P_{jk}^{hit}(i)}{i} = \int_{i=t}^{\infty} P_{jk}^{interv}(i), \tag{4}$$

where t is the time, $P_{jk}^{hit}=iP_{jk}^{interv}$ is the probability of a uniformly sampled point in time to be contained in an interval of length i. An average null waiting time distribution was then obtained by weighted averaging over the non-validation epochs (NV) epochs j:

$$\langle P_k^{null}(t)\rangle = \frac{\sum_{j\in NV} n_j^{spikes} P_{jk}^{null}(i)}{\sum_{j\in NV} n_j^{spikes}}, \tag{5}$$

where $n_j^{spikes}$ is the weighting factor, calculated as the total number of spikes detected in all channels in epoch j.

Average waiting time distributions were obtained as follows:

$$\langle P_k^{pre}(t)\rangle = \frac{\sum_{j\in NV} n_j^{spikes} P_{jk}^{pre}(i)}{\sum_{j\in NV} n_j^{spikes}}, \tag{6a}$$

$$\langle P_k^{post}(t)\rangle = \frac{\sum_{j\in NV} n_j^{spikes} P_{jk}^{post}(i)}{\sum_{j\in NV} n_j^{spikes}}. \tag{6b}$$

The reference family of functions $T_k^{(l)}(t-t_0)$, indexed by studied channel l, comprising a real function of scalp channel k and time t, centered around to was defined by:

$$T_{k,l}(t-t_0)=\log(\langle P_k^{post}(t)\rangle)-\log(\langle P_k^{null}(t)\rangle) \text{ for } t>t_0, \tag{7a}$$

$$T_{k,l}(t-t_0)=\log(\langle P_k^{pre}(t)\rangle)-\log(\langle P_k^{null}(t)\rangle) \text{ for } t<t_0, \tag{7b}$$

Figure 3:
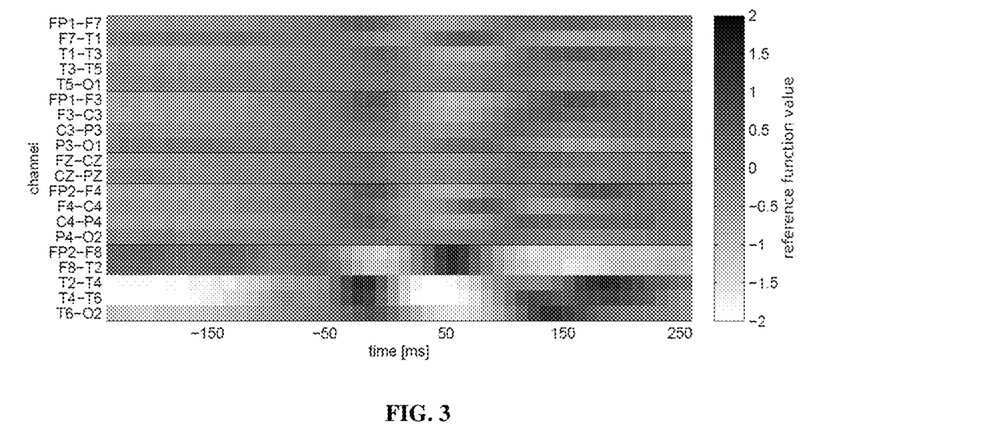
FIG. 3 is a graph, related to the results obtained in Example 1, shows for a selected subject with right temporal lobe epilepsy, a graphical representation of the reference function $T_k(t)$ as a function of the scalp channels comprising the standard bipolar montage and time.

The reference family of functions $\{T_l\}\equiv\{T_k^{(l)}(t-t_0)\}$ defined above was subsequently used according to the computer-implemented method of the present invention. The reference family of functions $\{T\}$ defined above was applied to the subjects' electroencephalographic recordings sequentially with 10 milliseconds increment of time $t_0$. A representative reference function derived from the electroencephalographic recordings of patients with temporal lobe epilepsy is shown in FIG. 3.

The matching score as a specific formulation of equation (1), was chosen:

$$S_l(t_0)=\Sigma_k T_{k,l}(t_k^{pre}(t_0)-t_0)+T_{k,l}(t_k^{post}(t_0)-t_0) \tag{8}$$

where $t_k^{pre}(t_0)$ and $t_k^{post}(t_0)$ denote the first zero-crossing present in the scalp channel k before and after the time $t_0$, respectively.

In order to validate the performance of the reference family of functions T derived for every intracranial channel l of a single subject (non-validation epochs), the computer-implemented method was used to detect intracranial interictal epileptiform discharges in the same subject basing on the subjects' scalp electroencephalographic signal alone.

Figure 4:
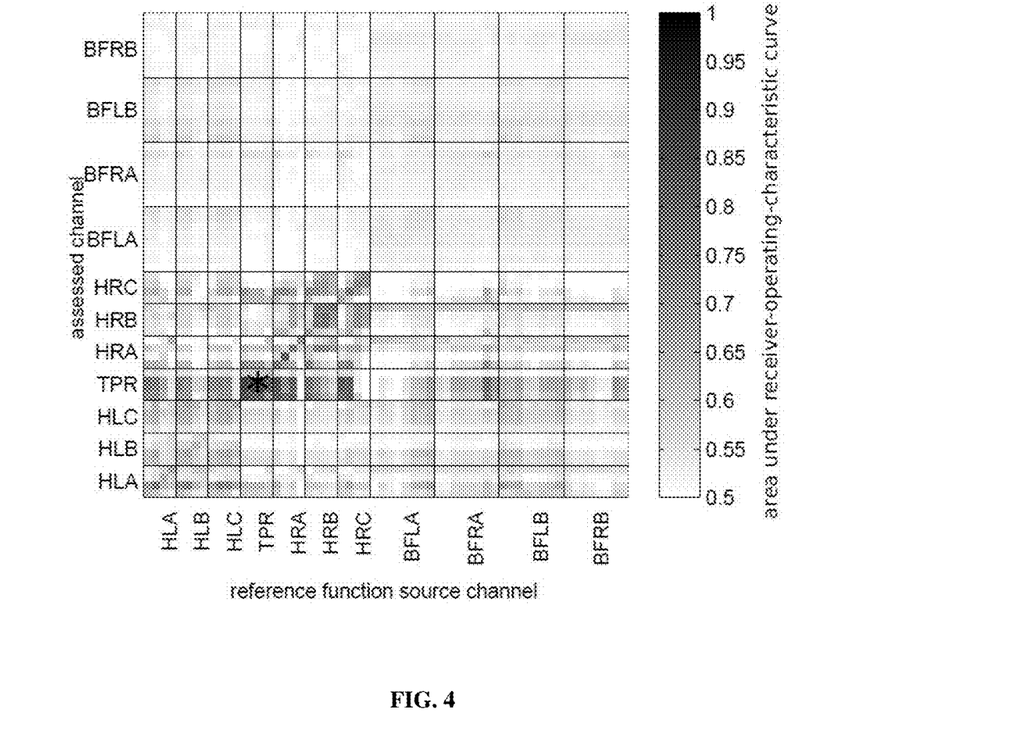
FIG. 4 related to the results obtained in Example 1, shows graphical representation of the matrix of values of the area under the receiving-operating-characteristic curve for each pair of intracranial channel l (from which the reference function is derived) and l' (for testing), $AUC(T^{(l)}, l')$. The optimal combination between the reference function and the assessed intracranial channel is marked by an asterisk on the related matrix of values.
Figure 5:
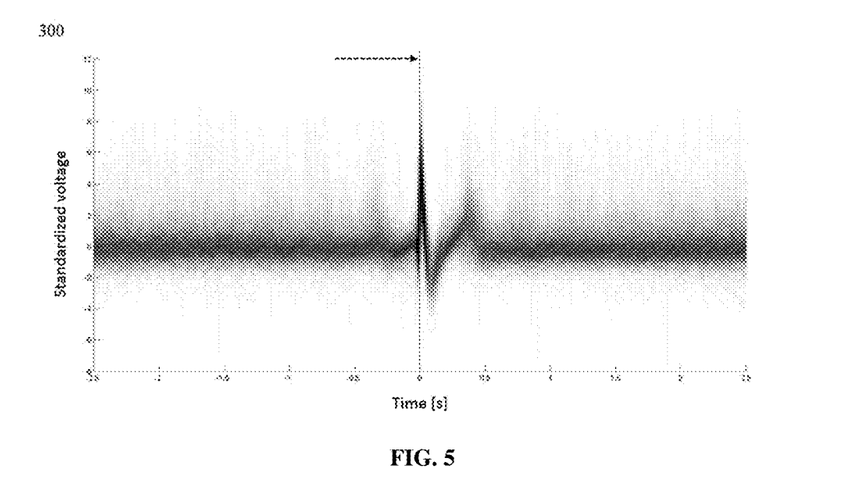
FIG. 5 is a graph related to the results obtained in Example 1, showing, for a selected subject with right temporal lobe epilepsy, and the optimal combination between the reference function and the assessed intracranial channel, an overlay of intracranial voltage signals corresponding to detections performed by applying this optional reference function to the simultaneous scalp electroencephalographic signal.

The computer-implemented method using the reference family of functions $\{T\}$ so designed, was applied to scalp channels of the epochs in the validation subset $V_1$ of the same subject from which the reference family of functions $\{T\}$ was derived. The matching score $S^{(l)}(t)$ produced by each of the reference functions $T^{(l)}\in\{T\}$ was assessed for its efficiency in detecting intracranial spikes, within the framework of receiving-operating-characteristic analysis. More specifically, the matching score $S^{(l)}(t)$ calculated on the scalp channels for each consecutive 10 millisecond time window was used for binary classification of whether said time window contains or not an intracranial spike (8) in an intracranial channel l'. For each pair of intracranial channels l (for which the reference function $T^{(l)}$ was derived) and l' (for assessment) a respective value of the area under the receiving-operating-characteristic curve was obtained, producing a matrix of values. An example of said matrix is represented in FIG. 4. The graph in FIG. 5 shows, for a selected subject with right temporal lobe epilepsy, and the optimal combination between the reference function $T_l$ and the assessed intracranial channel, an overlay of intracranial voltage signals corresponding to detections performed by applying the optimal reference function to the simultaneous scalp electroencephalographic signal. The optimal combination between the reference function and the assessed intracranial channel, is marked by an asterisk on the related matrix of values in FIG. 4.

For each studied subject, the optimal area under the receiving-operating-characteristic curve value was estimated, according to the following equation:

$$AUC^{opt}=\max_{l,l'} AUC(l,l'), \tag{9}$$

Furthermore, in order to estimate the robustness of the computer-implemented method of the present invention, cross-validation was performed by using the computer-implemented method for one subject implementing a reference family of functions derived from others subjects.

For this purpose, a family of 22 validation reference functions $\{T\}$ was selected from a set comprising all the 964 reference functions (one for every studied intracranial channel l). The reference functions $T_l$ comprising said family $\{T^*\}$ satisfied the following two conditions:

$$\max_{l'} AUC(T_l, l') > 0.8, \quad (10a)$$

$$\left(\frac{1}{|NV|}\sum_{j \in NV} n_{ij}^{spike}\right) > 1, \quad (10b)$$

where |NV| is the number of non-validation epochs and the sum runs over said non-validation epochs.

The first condition (10a) imposes the existence of at least one intracranial channel l' for which a reference function $T^{(l)} \in \{T^*\}$ detected spikes with a value of the area under the receiving-operating-characteristic curve superior to 0.8 when applied to the data ($V_1$ epoch subset) obtained from the same subject from which the reference function TC was derived. The second condition (10b) was imposed so that the minimum interictal epileptiform discharge detection rate in the intracranial channel l from which a reference function $T^{(l)}$ was derived was more than one interictal epileptiform discharge detected per epoch, on average (NV epoch subset).

For each subject the validation reference family of functions $T^{(l)} \in \{T^*\}$ was applied to the validation subsets $V_2$ and the resultant set of matching scores $S^{(l)}(t)$ was used to calculate a composite matching score $S^*(t)$, defined as follows:

$$S^*(t) = \max_{l \in \{currently\ assessed\ subj.\}} S_l(t). \quad (11)$$

According to equation (11), said composite matching score $S^*(t)$ is, for every point in time, the maximum of the matching scores produced by all functions in the reference family of functions $\{T^*\}$ with the exception of reference functions that were derived from channels of the currently assessed subject.

The composite matching score $S^*(t)$ was assessed for binary classification of whether or not within consecutive 10 millisecond wide window centered at time t an intracranially detected spike is present in a given channel l' of the assessed subject. For each subject the channel-wise maximum area under the receiving-operating-characteristic curve was identified:

$$AUC^{val} = \max_{l'} AUC(\{T^*\}, l'). \quad (12)$$

Results

Within the present group of 16 subjects the optimal area under the receiving-operating-characteristic curve $AUC^{opt}$ values ranged from 0.63 to 0.99, with a mean value of 0.83.

Within the present group of 16 subjects the validated channel-wise maximum area under the receiving-operating-characteristic curve values $AUC^{val}$ ranged from 0.53 to 0.81, with a mean value of 0.70.

Figure 6:
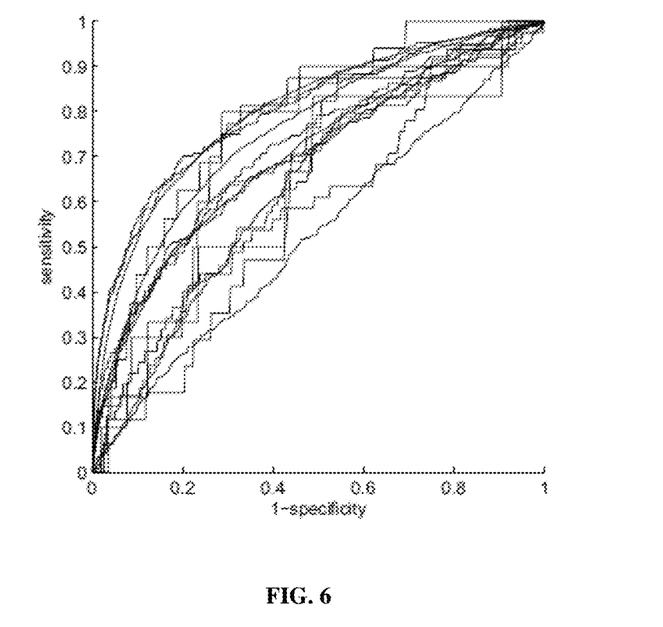
FIG. 6 is a graph related to the results obtained in Example 1, showing the receiving-operating-characteristic curves obtained for the 16 subjects by applying the validation reference family of functions $\{T^*\}$.
Figure 7:
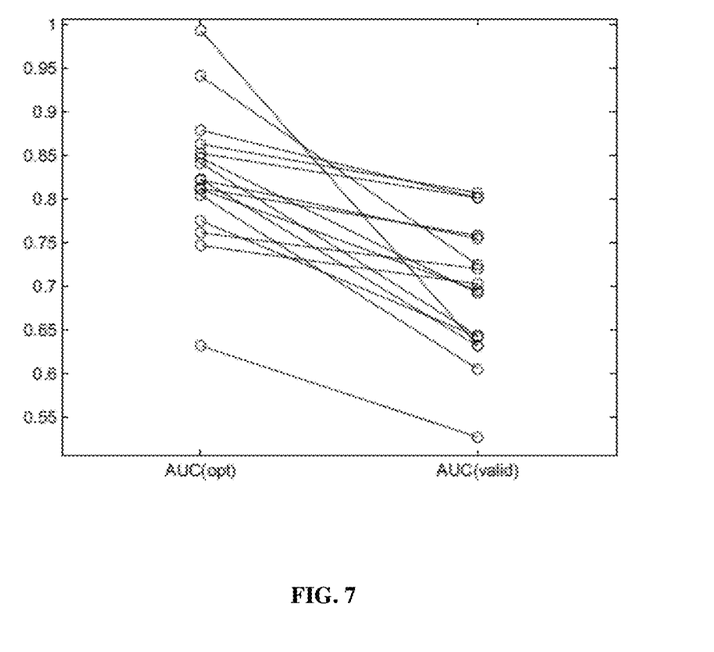
FIG. 7 is a graph related to the results obtained in Example 1, showing the relationship, for each of the 16 studied subjects, between the areas under the receiving-operating-characteristic curve for the optimal within-subject combination of the reference function and the assessed intracranial channel ($AUC_{opt}$) to those obtained by applying the validation reference family of functions $\{T^*\}$ ($AUC_{valid}$).

Detailed values of said channel-wise maximum receiving-operating-characteristic curves and said optimal area under the receiving-operating-characteristic curves are presented in Table 2. The associated receiving-operating-characteristic curves are shown in FIG. 6. The relationship between the channel-wise maximum receiving-operating-characteristic curves and the optimal area under the receiving-operating-characteristic curve is shown in FIG. 7.

TABLE 2

| Patient | $AUC^{opt}$ | $AUC^{val}$ |
|---|---|---|
| 1 | 0.8786 | 0.8011 |
| 2 | 0.8109 | 0.6949 |
| 3 | 0.7611 | 0.7197 |
| 4 | 0.8216 | 0.7543 |
| 5 | 0.8627 | 0.8067 |
| 6 | 0.9929 | 0.6318 |
| 7 | 0.8408 | 0.6431 |
| 8 | 0.8225 | 0.6315 |
| 9 | 0.8121 | 0.7578 |
| 10 | 0.8522 | 0.8011 |
| 11 | 0.8470 | 0.6922 |
| 12 | 0.8042 | 0.6049 |
| 13 | 0.7749 | 0.6419 |
| 14 | 0.7465 | 0.7024 |
| 15 | 0.9407 | 0.7243 |
| 16 | 0.6316 | 0.5268 |

Example 2

Materials and Methods

Material

The computer-implemented method according to the present invention was used to detect pathological brain activity patterns in further 37 subjects. Said 37 subjects present either temporal (n=22) or extratemporal (n=15, e.g. focal frontal, parietal or occipital) epilepsy with strictly unilateral epileptic focus location. In this Example, the reference family of functions that was constructed in Example 1 was used, after appropriate modifications, to allow for discrimination of temporal from extratemporal epilepsy patients. The 37 prerecorded scalp electroencephalographic signals of 60 minute length were chosen from the "Epilepsiae" medical database and were not used in Example 1. Intracranial signals were not used in this example. As in Example 1, only patients with full 10-20 scalp electrodes coverage supplemented with true anterior-temporal electrodes (T1 and T2) were included in this example.

The clinical and demographic details of the subjects are specified in the Table 3 below:

TABLE 3

| Patient | Gender | Age | Age at epilepsy onset | Focus location | Etiology |
|---|---|---|---|---|---|
| 1 | male | 17 | 0 | Left temporal | Hippocampal sclerosis |
| 2 | female | 31 | 18 | Right occipital | Malformation |
| 3 | female | 17 | 8 | Left temporal | Unknown |
| 4 | female | 48 | 7 | Left frontal | Malformation |
| 5 | male | 41 | 21 | Right temporal | Hippocampal sclerosis, postinfecious |
| 6 | male | 56 | 6 | Right temporal | Hippocampal sclerosis |
| 7 | male | 42 | 0 | Left central | Cryptogenic |
| 8 | female | 32 | 4 | Right frontal | Cryptogenic |
| 9 | female | 22 | 31 | Right temporal | Hippocampal sclerosis |
| 10 | male | 31 | 8 | Right frontal | Hippocampal sclerosis |
| 11 | male | 24 | 5 | Left extratemporal | Hippocampal sclerosis |
| 12 | male | 47 | 44 | Left temporal | Malformation |
| 13 | male | 26 | 8 | Left frontal | Unknown |
| 14 | male | 36 | 36 | Left temporal | Tumor |
| 15 | male | 65 | 15 | Left temporal | Malformation, hippocampal sclerosis |

TABLE 3-continued

| Patient | Gender | Age | Age at epilepsy onset | Focus location | Etiology |
|---|---|---|---|---|---|
| 16 | female | 50 | 7 | Right frontal | Hippocampal sclerosis, cryptogenic |
| 17 | female | 15 | 13 | Right temporal | Malformation, hippocampal sclerosis |
| 18 | male | 43 | 2 | Left temporal | Hippocampal sclerosis |
| 19 | female | 61 | 13 | Left temporal | Hippocampal sclerosis |
| 20 | male | 32 | 17 | Left temporal | Tumor |
| 21 | male | 47 | 17 | Right temporal | Malformation |
| 22 | male | 51 | 3 | Right temporal | Cryptogenic |
| 23 | male | 13 | 10 | Right temporal | Tumor |
| 24 | female | 34 | 18 | Left frontal | Malformation |
| 25 | male | 41 | 5 | Right temporal | Cryptogenic |
| 26 | female | 65 | 17 | Left frontal | Malformation |
| 27 | female | 54 | 4 | Left temporal | Hippocampal sclerosis |
| 28 | female | 16 | 4 | Left frontal | Malformation |
| 29 | female | 67 | 23 | Left temporal | Cryptogenic |
| 30 | male | 38 | 3 | Right parietal | Malformation |
| 31 | male | 39 | 8 | Left frontal-central | Cryptogenic |
| 32 | male | 67 | 40 | Left temporal | cryptogenic |
| 33 | male | 50 | 43 | Right temporal | Unknown |
| 34 | female | 37 | 29 | Right temporal | hippocampal sclerosis |
| 35 | female | 50 | 13 | Left temporal | hippocampal sclerosis |
| 36 | male | 36 | 2 | Left temporal | cryptogenic |
| 37 | male | 39 | 3 | Right temporal | malformation hippocampal sclerosis |

Methods

As starting point for the analysis was chosen the family of 22 validation reference functions $\{T^*\}$ derived in Example 1. Another family of reference functions $\{T^{**}\}$ was then derived by applying the following transformation to each of the reference function $T \in \{T^*\}$:

$$F(T) \equiv F : \left\{ T_k(t) \rightarrow -T_{f(k)}(t) \bigg|_k^{\forall} \right\}, \quad (13a)$$

where t is time, k is the channel name and f(k) is a transformation of channel name specified below:

$$f : \begin{cases} Fp1 \rightarrow Fp2 & Fp1 \rightarrow Fp2 \\ F3 \rightarrow F4 & F4 \rightarrow F3 \\ F7 \rightarrow F8 & F8 \rightarrow F7 \\ T3 \rightarrow T4 & T4 \rightarrow T3 \\ T5 \rightarrow T6 & T6 \rightarrow T5 \\ C3 \rightarrow C4 & C4 \rightarrow C3 \\ P3 \rightarrow P4 & P4 \rightarrow P3 \\ O1 \rightarrow O2 & O2 \rightarrow O1 \\ T1 \rightarrow T2 & T2 \rightarrow T1 \\ Fz \rightarrow Fz & Cz \rightarrow Cz \\ Pz \rightarrow Pz \end{cases} \quad (13b)$$

and for a bipolar channel pair [k, k']:

$$f([k,k'])=[f(k),f(k')]. \quad (13c)$$

As shown in equation (13a), said transformation produced a transposed version of the initial reference function $T_k$ by substituting a symmetric channel f(k) to each channel k. The application of the transformation F to the functions in $\{T^*\}$ is an example of heuristic manipulation of the reference family of functions in the designing process.

It has be noticed that none of the assesed subjects' recordings were used for the derivation of these reference families of functions.

The matching score as a specific formulation of equation (1), was chosen again:

$$S_T(t) = \Sigma_k T_k(t_k^{pre}(t)-t) + T_k(t_k^{post}(t)-t), \quad (14)$$

where T is the reference function used for the calculation of the score $S_T$, $t_k^{pre}(t_0)$ and $t_k^{post}(t_0)$ denote the first zero-crossing present in the scalp channel k respectively before and after the time $t_0$. A compound cumulative matching score $S^{}(t)$ was defined for $$S_T^{}(t) = \int_0^t S_T(t_0) + S_{F(T)}(t_0) dt_0 \quad (15)$$

This is an example of a cummulative matching score and of how a matching score can be defined for two reference functions $T \in \{T^*\}$ and $F(T) \in \{T^{**}\}$ belonging to two different reference families of functions.

The cummulative matching score for fixed values of t was then assessed in the framework of receiver-operating-characteristic analysis for its capability of distinguishing between electroencephalographic recordings of temporal and extratemporal subjects.

Results

The cummulative matching score performed differently for different reference functions $T \in \{T^*\}$ together with their respective transformed variants $F(T) \in \{T^{**}\}$. For 60 minute recordings 5 reference functions, out of 22 analyzed reference functions, produced area under receiver-operating-characteristic curve values greater than 0.65 and the maximum area under receiver-operating-characteristic curve value obtained was 0.71. These results confirm the potential applicability of the method for this classification problem.

Figure 8:
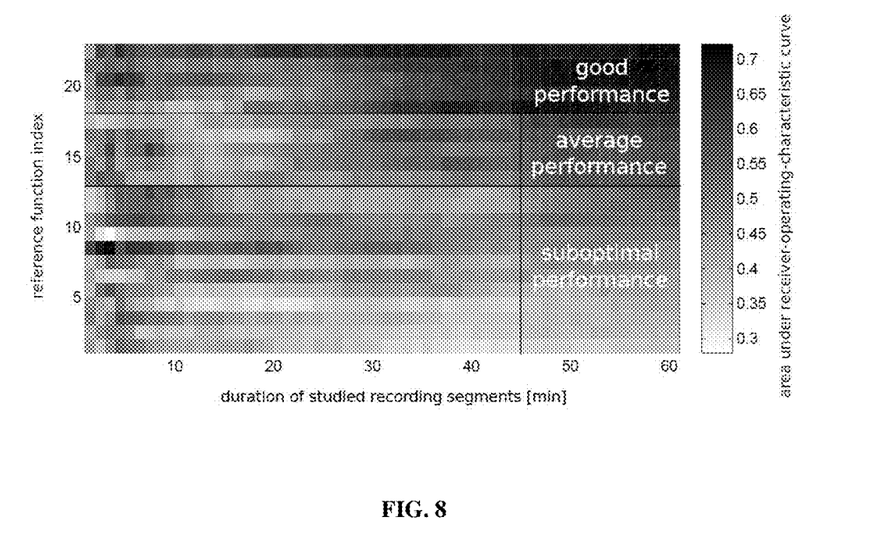
FIG. 8 is a graph related to the results obtained in Example 2, showing the reference function sorted along the vertical axis according to their performances estimated from the area under receiver-operating-characteristic curve as function of full-length recording along the horizontal axis.
Figure 9:
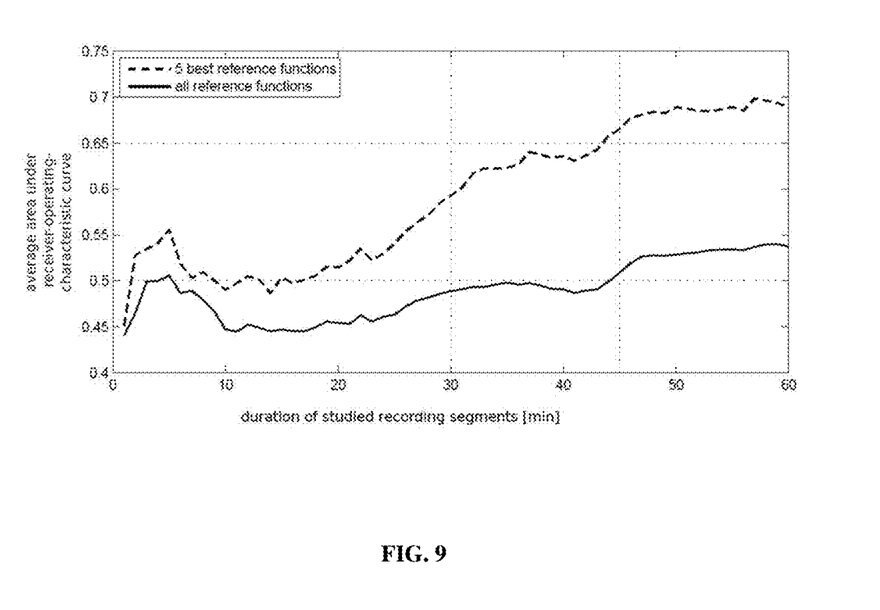
FIG. 9 is a graph, related to the results obtained in Example 2, showing the average value of area under receiver-operating-characteristic curve as a function of recording length considering all reference functions or the subset of 5 reference functions having area under receiver-operating-characteristic curve values greater than 0.65 for full-length recordings.

FIG. 8 and FIG. 9 show the dependence of the area under receiver-operating-characteristic curve values for different reference function on the length of recordings studied. In FIG. 8 the reference functions have been sorted along the vertical axis according to their performance estimated form the area under receiver-operating-characteristic curve as a function of full-length recordings. It can be seen that stable performance is obtained for recording length of more than 30-45 minutes with significant fluctuations if recording length was less than 20 minutes. FIG. 9 shows average area under receiver-operating-characteristic curve values as a function of recording length considering all reference functions or the subset of 5 reference functions having area under receiver-operating-characteristic curve values greater than 0.65 for full-length recordings. Significant improvement of classification performance can be noticed for recording length higher then 20-30 minutes.

The invention claimed is:

1. A computer-implemented method for detecting brain activity patterns from a scalp electroencephalographic signal, the method comprising the steps of:
   a) obtaining electroencephalographic signals as a function of multiple channels and time;
   b) identifying, for each channel, the zero-crossings of its corresponding electroencephalographic signal over a fixed threshold;
   c) generating a zero-crossing representation of the electroencephalographic signals with the identified zero-crossings;

d) obtaining at least one reference family of functions of time and channels from a zero-crossing statistical analysis of a zero-crossing representation of pre-recorded electroencephalographic signals, the functions of the at least one reference family of functions being real functions;

e) for each segment of a plurality of segments of the generated zero-crossing representation, calculating a corresponding matching score by comparing said zero-crossing representation of the segment with at least one reference function from the at least one reference family of functions;

f) monitoring an evolution of the matching score over time based on a set of matching scores for successive segments of the generated zero-crossing representation;

wherein, for each segment, the corresponding matching score relative to a zero-crossing representation of a segment for one reference function T centered in $t_0$ is defined by the formula:

$$S_T(t_0) = \Sigma_{k \, \epsilon K} \Sigma_{t \epsilon \phi(k, t_0)} T_k(t-t_0),$$

wherein $S_T(t_0)$ is the matching score, the first sum runs over the set of channels k εK, and the second sum runs over a defined subset t εφ(k, $t_0$) of zero-crossings for each channel k of the segment surrounding $t_0$; and g) determining a state of the brain based on the evolution of the matching score.

2. The method according to claim 1, wherein said step of obtaining the at least one reference family of functions comprises the steps:

i. obtaining recordings of at least two electroencephalographic signals, wherein each electroencephalographic signal is a scalp electroencephalographic signal or an intracranial electroencephalographic signal of predefined length, wherein the recordings of at least two electroencephalographic signals are simultaneous to each other;

ii. performing the zero-crossing statistical analysis for each obtained electroencephalographic signal recording with respect to at least one feature of the obtained recordings; and iii. computing the at least one reference family of functions from the zero-crossing statistical analysis.

3. The method according to claim 1, further comprising a step of evaluating the matching scores by setting a binary criterion on the matching scores.

4. The method according to claim 3, wherein the method differentiates a normal electroencephalographic signal from an electroencephalographic signal comprising pathological brain activity patterns.

5. The method according to claim 4, wherein differentiation between a normal electroencephalographic signal and an electroencephalographic signal comprising pathological brain activity patterns is performed in real time.

6. The method according to claim 1, wherein the step b) is preceded by a filtering step comprising filtering the electroencephalographic signals with a zero-phase shift bandpass filter.

7. The method according to claim 6, wherein the filtering step is followed by the step of dividing the electroencephalographic signals into non-overlapping consecutive segments of fixed length.

8. The method according to claim 1, wherein each matching score is calculated for a set of functions belonging to one reference family of functions, producing a respectively indexed set of matching scores for any given $t_0$.

9. The method according to claim 1, wherein matching scores calculated for a continuously indexed reference family of functions results in matching scores that are each a function of a time $t_0$.

10. The method according to claim 1, wherein the step of calculating each matching score includes comparing said zero-crossing representation of a corresponding segment of the generated zero-crossing representation with two reference functions issued from two different reference families of functions.

11. The method according to claim 1, wherein the step of obtaining at least one reference family of functions comprises the steps of:

obtaining recordings of at least one scalp electroencephalographic signal of predefined length; and deriving at least one reference family of functions by optimizing the parameters of a mathematical function according to characteristics of the obtained electroencephalographic signal recordings.

12. A system for detecting brain activity patterns, the system comprising a data processing system configured to:

a) obtain electroencephalographic signals as a function of multiple channels and time;

b) identify, for each channel, the zero-crossings of its corresponding electroencephalographic signal over a fixed threshold;

c) generate a zero-crossing representation of the electroencephalographic signals with the identified zero-crossings;

d) obtain at least one reference family of functions of time and channels from a zero-crossing statistical analysis of a zero-crossing representation of pre-recorded electroencephalographic signals, the functions of the at least one reference family of functions being real functions;

e) for each segment of a plurality of segments of the generated zero-crossing representation, calculate a corresponding matching score by comparing said zero-crossing representation of the segment with at least one reference function from the at least one reference family of functions;

f) monitor an evolution of the matching score over time based on a set of calculated matching scores for successive segments of the generated zero-crossing representation;

wherein, for each segment, the corresponding matching score relative to a zero-crossing representation of a segment for one reference function T centered in $t_0$ is defined by the formula:

$$S_T(t_0) = \Sigma_{k \, \epsilon K} \Sigma_{t \epsilon \phi(k, t_0)} T_k(t-t_0),$$

wherein $S_T(t_0)$ is the matching score, the first sum runs over the set of channels k εK, and the second sum runs over a defined subset t εφ(k, $t_0$) of zero-crossings for each channel k of the segment surrounding $t_0$; and g) determine a state of the brain based on the evolution of the matching score.

13. The system according to claim 12, wherein, to obtain the at least one reference family of functions, the data processing system is further configured to:

i. obtain recordings of at least two electroencephalographic signals of predefined length, wherein each electroencephalographic signal is a scalp electroencephalographic signal or an intracranial electroencephalographic signal, and wherein the recordings of at least two electroencephalographic signals are simultaneous to each other;

ii. perform the zero-crossing statistical analysis for each obtained electroencephalographic signal recording with respect to at least one feature of the obtained recordings; and iii. compute the at least one reference family of functions from the zero-crossing statistical analysis.

14. A non-transitory computer program product for detecting brain activity patterns, the computer program product comprising instructions which, when the instructions are executed by a computer, cause the computer to carry out a method comprising the steps of:

a) obtaining electroencephalographic signals as a function of multiple channels and time;

b) identifying, for each channel, the zero-crossings of its corresponding electroencephalographic signals over a fixed threshold;

c) generating a zero-crossing representation of the electroencephalographic signals with the identified zero-crossings;

d) obtaining at least one reference family of functions of time and channels from a zero-crossing statistical analysis of a zero-crossing representation of pre-recorded electroencephalographic signals, the functions of the at least one reference family of functions being real functions;

e) for each segment of a plurality of segments of the generated zero-crossing representation, calculating a corresponding matching score by comparing said zero-crossing representation of the segment with at least one reference function from the at least one reference family of functions;

f) monitoring an evolution of the matching score over time based on a set of matching scores for successive segments of the generated zero-crossing representation;

wherein, for each segment, the corresponding matching score relative to a zero-crossing representation of a segment for one reference function T centered in $t_0$ is defined by the formula:

$$S_T(t_0) = \Sigma_{k \, \epsilon K} \Sigma_{t \epsilon \phi(k, t_0)} T_k(t-t_0),$$

wherein $S_T(t_0)$ is the matching score, the first sum runs over the set of channels k εK, and the second sum runs over a defined subset t εφ(k, $t_0$) of zero-crossings for each channel k of the segment surrounding $t_0$; and g) determining a state of the brain based on the evolution of the matching score.

15. A non-transitory computer-readable storage medium comprising instructions which, when the instructions are executed by a computer, cause the computer to carry out a method comprising the steps of:

a) obtaining electroencephalographic signals as a function of multiple channels and time;

b) identifying, for each channel, the zero-crossings of its corresponding electroencephalographic signal over a fixed threshold;

c) generating a zero-crossing representation of the electroencephalographic signals with the identified zero-crossings;

d) obtaining at least one reference family of functions of time and channels from a zero-crossing statistical analysis of a zero-crossing representation of pre-recorded electroencephalographic signals, the functions of the at least one reference family of functions being real functions;

e) for each segment of a plurality of segments of the generated zero-crossing representation, calculating a corresponding matching score by comparing said zero-crossing representation of the segment with at least one reference function from the at least one reference family of functions;

f) monitoring an evolution of the matching score over time based on a set of matching scores for successive segments of the generated zero-crossing representation;

wherein, for each segment, the corresponding matching score relative to a zero-crossing representation of a segment for one reference function T centered in $t_0$ is defined by the formula:

$$S_T(t_0) = \Sigma_{k \, \epsilon K} \Sigma_{t \epsilon \phi(k, t_0)} T_k(t-t_0),$$

wherein $S_T(t_0)$ is the matching score, the first sum runs over the set of channels k εK, and the second sum runs over a defined subset t εφ(k, $t_0$) of zero-crossings for each channel k of the segment surrounding $t_0$; and g) determining a state of the brain based on the evolution of the matching score.

16. The computer-readable storage medium according to claim 15, wherein the computer-readable storage medium further comprises the at least one reference family of functions.

\* \* \* \* \*